(12) United States Patent
Bakshi

(10) Patent No.: US 7,632,976 B2
(45) Date of Patent: Dec. 15, 2009

(54) LOW COST SELECTIVE OCTENE PROCESS: RHT-OCTENE

(76) Inventor: Amarjit Singh Bakshi, 20130 Chateau Bend Dr., Katy, TX (US) 77450

(*) Notice: Subject to any disclaimer, the term of this patent is extended or adjusted under 35 U.S.C. 154(b) by 522 days.

(21) Appl. No.: 11/540,179

(22) Filed: Sep. 29, 2006

(65) Prior Publication Data
US 2008/0081939 A1 Apr. 3, 2008

(51) Int. Cl.
*C07C 2/08* (2006.01)
(52) U.S. Cl. .................. 585/510; 585/518; 585/519; 585/520; 585/531; 585/533
(58) Field of Classification Search .......... 585/500, 585/502, 510, 518, 519, 520, 530, 531, 532, 585/533
See application file for complete search history.

(56) References Cited

U.S. PATENT DOCUMENTS 6,042,798 A * 3/2000 Masuda et al. ............ 585/820
7,196,238 B2 * 3/2007 Nurminen et al. ......... 585/517
7,259,123 B2 * 8/2007 De Boer et al. ........... 585/513

* cited by examiner

*Primary Examiner*—Glenn Caldarola
*Assistant Examiner*—Randy Boyer

(57) ABSTRACT

This invention covers a process for making Octene from nix $C_4$ Feed by a low cost highly selective multistage process. The multi staging of reactors essentially provides lower cost than conventional processes. Two options are provided in FIGS. 1 and 2 as regards to configuration based on the same catalyst but as can be seen that FIG. 1 configuration is low cost option with very high selectivity. The process provides conversion of butene to Octene >95% and product purity >96%. Product can be fractionated and can have a high purity Octene product by removing the trimers/polymers from the octene product. As mentioned due to the nature of the process configuration, one achieves high yield and selectivity with low cost.

13 Claims, 2 Drawing Sheets

RHT Octene Process

RHT Octene Process

RHT Octene Process

LOW COST SELECTIVE OCTENE PROCESS: RHT-OCTENE

FIELD OF THE INVENTION

The invention relates to producing Octene from a mixed $C_4$ feed stream by using a unique configuration and reactors provided as multistage operation so as increase the yield and selectivity at low cost. The process is designed to dimerize the n-butene selectively to Octene. Small amounts of trimers/polymers are also made during the reaction, but they are less than 5.0% by wt. To get the high Octene purity, one can remove the Trimers and have high purity octene if so required. The octene reaction converts all the three species of n-butene (butene-1, cis-butene-2 and trans-butene-2) to octene. The configuration provides capability to do the fractionation an reaction at optimum conditions and also to have best selectivity at octene and very small trimers are formed. The catalyst used in this application is Zeolite or Zeolite/Pt but not limited to (use of any other suitable catalyst in the market will be practiced), so as to get the best yield and selectivity.

BACKGROUND OF THE INVENTION

RHT-Octene process is based on dimerizing the n-butene in the feed to Octene selectivity and at low temperatures so as to get the maximum equilibrium conversions. The fixed bed reactors are used in this service in down flow or up flow mode (preferably down flow) in single phase or two-phase operation. The Fractionator is operated in the range of 75 to 100 psig. The side draws are taken where maximum amount of n-butene is present and are pumped to the reactor pressure. Reactors are operated in down flow or up flow mode and also are capable of single phase or two phase operation, and temperature of about 240 to 450 F (preferably 280 to 350 F) and pressure of about 250 to 450 psig in the reactor (preferably 370 400 psig) but consistent with equilibrium conditions based on the temperature so that the feed is not more than 10% in vapor phase, preferably in liquid single phase. The reactor effluent is sent to the Octene column for separation of octene and $C_4$-S. The process is capable of taking ethylene feed directly to the reactor and converting it to the Octene-1. The reactor effluent is sent to the fractionator for separation of Octene-1 and other components.

The process is based on Zeolite catalyst application with multistage reactor design so as to get the best selectivity and yield at low cost. Octene-1 is used as co-monomer in the Polyethylene process.

$C_4$ processing is a major requirement for both petrochemical and refiners. Though ethylene being the major building block in petrochemical chain and the Octene-1 being one of the co-monomer for the polyethylene, others being butene-1 and hexene-1. RHT has taken major interest in this area and is coming up unique configuration for the application at low cost and having the best selectivity and yields.

RHT has in figure shown another unique configuration by installing bulk catalyst in the column; details of this will be explained in sections where all the art is detailed as per the figures.

SUMMARY OF THE INVENTION

The process in this art claims that n-Butene or Ethylene can be converted to Octene/Octene-1 by a unique multistage reactor configuration or bulk catalyst in the column configuration as will be illustrated in the FIGS. 1 and 2, at low cost with high selectivity and yield.

The process in this art claims that feed of n-butenes or ethylene can be converted to octene/octene-1 in the unique process configuration at moderate operating conditions. The process is designed so that the fractionator and reactors can work at different conditions so as to provide optimum conditions for reaction and fractionation. This multistage unique technique is capable of providing the best conditions for each unit operation.

The art claims that Zeolite catalyst, Zeolite/Pt or any other catalyst available in market will be used for the process that provides the best selectivity and cost advantages for the reaction and the process economics.

The art in the process is of the unique configurations and also the reactor design that provides the low cost option for the process. The reactors are designed for down flow or up flow single or two-phase operation with optimum conditions.

The art of the process also provides a unique method to install bulk catalyst in the column as shown in FIG. 2, which removes most of the disadvantages of Reactive distillation which has used cumbersome catalyst technique for installation and cost of the catalyst increases due to packaging and labor for loading the catalyst in the packing and column.

These unique features will be apparent to one who is skilled in the art from the figures and claims and brief description of the FIGS. 1 and 2.

The art also claims that in this process ethylene feed in vapor phase at about 450 psig comes from Battery limit and after cleaning in the absorber bed item 9 it is heated with the product stream 4, and further heated to about 210 to 250 F and is fed to reactors in parallel item 8, and reactor effluent is fed to the fractionator. In this application the fractionator is operated at 150 to 300 psig, and vapor stream is taken as overhead product which can be recycled after recovery. The bottom product is Octene-1 and is sent to storage. The people in the art will be able to see the merits of the process and see the optimization potential that will be provided in design of the unit.

Figure 2:
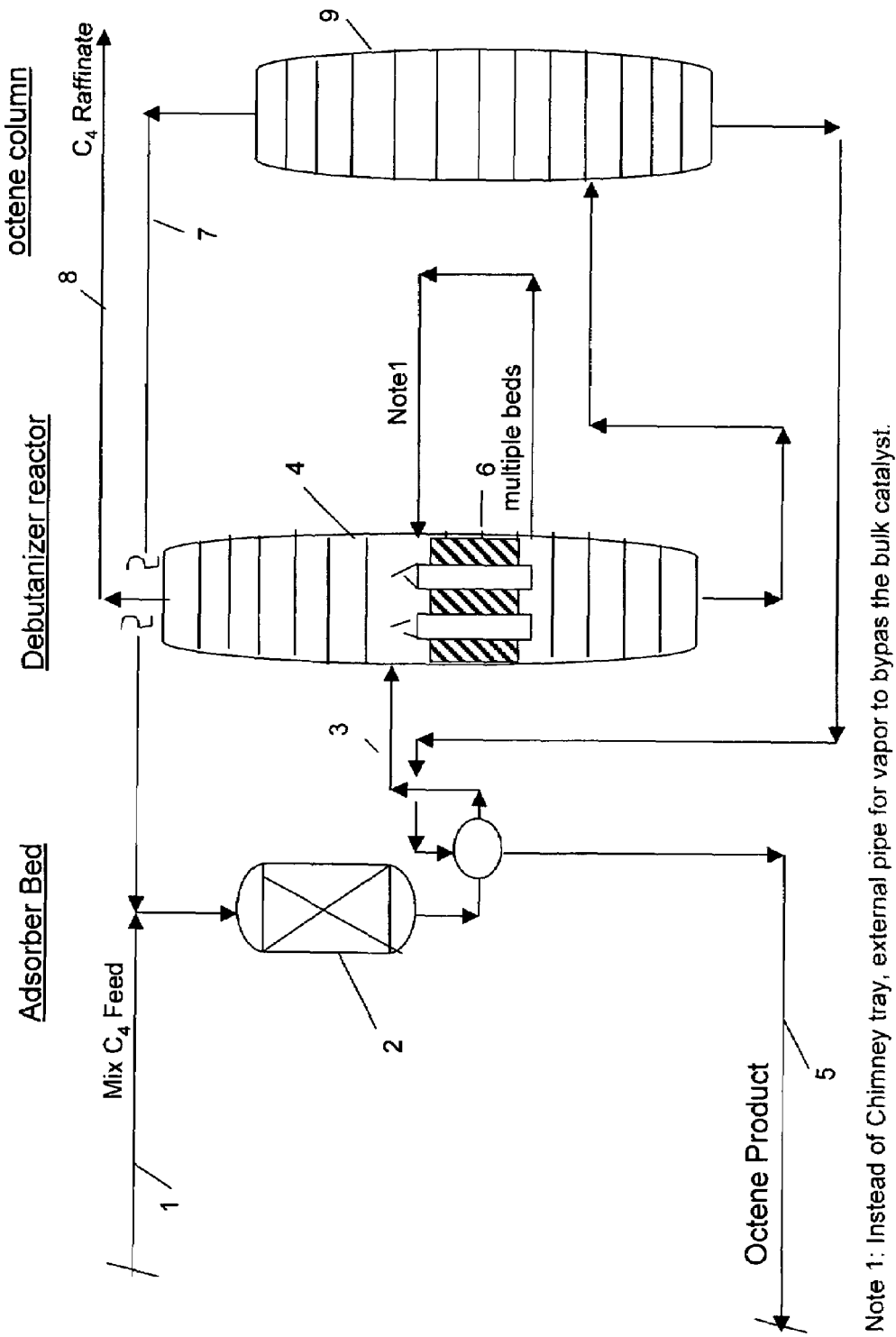

FIG. 2 is alternate mode of the simple process flow diagram of the above flow scheme and all things are same except the reactor configuration, which is bulk catalyst in the column. The feed at the same conditions as to other reactor 380 psig and 260 to 300 F is fed to Debutanizer reactor column item 4, after going through absorber bed item 2, so as to remove the impurities. The feed is heated in the Feed/Product exchanger and is fed to the Debutanizer Reactor column 4, at about 250 F on the Multiple beds of catalyst in the column item 5, is provided so as to improve the selectively. The technique of vapor bypass by chimney tray or external pipe can be used. The Debutanizer reactor item 4 operates in this case at about 350 to 400 psig. Some of unreacted C4's are taken with the bottom octene product so as to keep the bottom temperature low. The octene separation is done in the Octene column item 9, where octene is taken from bottom stream 5 and the unreacted C4's are recovered overhead item 7, and recycled to the Feed. The Debuanizer Reactor Column Item 4, overhead stream is taken C4 raffinate and is sent to the battery limit, this configuration is not suitable for Ethylene conversion to octene.

DETAILED DESCRIPTION OF THE INVENTION

Figure 1:
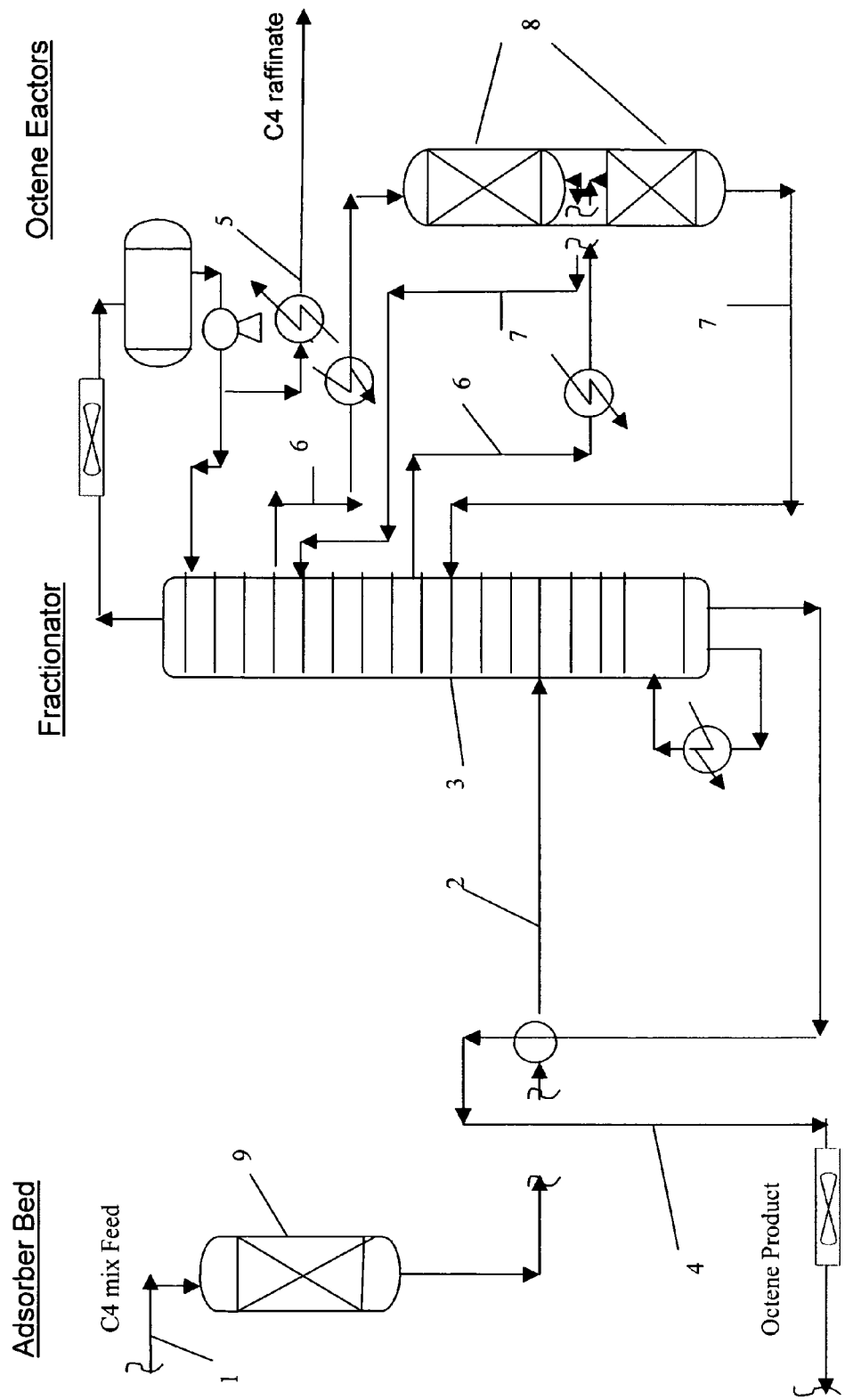
FIG. 1 is simplified process flow diagram of the process, where the $C_4$ mix feed (which has already been washed with caustic to remove sulfur) is pumped from storage to the operating pressure of about 100 psig stream 1. The Stream 1 goes through a absorber bed item 9, which removes any impurities which will deactivate the catalyst, basic compounds like residual caustic and heavy metals like iron, Na, K and arsenic. The stream 2 after heating with the product is fed to the column item 3. The $C_4$'s are driven overhead and are taken as side draw where the n-butene concentration is maximum. The side draws streams 6 is heated to the reactor temperature of 280 to 350 F and pressure of about 400 psig, and are fed to the reactor item 8. The reaction of n-butene to octene is performed at WHSV of 2 to 4 (WHSV of 2 is enough to provide high conversions of over 95%). As two reactors are being used to multistage for high selectivity and yield, hence WHSV is about 4 is good for each reactor. The operating conditions for both the reactors are the same. The reactor effluent stream 7 is fed back to the column at the same location as shown in the FIG. 1, so as to fractionate the reactor effluents and octene is taken as bottom product and $C_4$ inerts, lighter olefins and other unreacted $C_4$'s are taken as overhead raffinate product. From this unique configuration one expects a conversion of over 95% to octene and also selectivity of about 95%. If higher purity octene product is required the product can be fractionated to remove the trimers/polymers as heavy's drag stream and take the octene product overhead at high purity.

The major art and know how described here is a disclosure of producing Octene/Octene-1, with the n-butene or ethylene feed as described above and convert it to octene by unique process configuration as described in FIGS. 1 and 2 (for n-butene feed). This provides low cost, highly selective and high conversion process. This highly selective option and conversion over 95% and purity over 95%, which can be further improved by further distillation to remove the drag stream of trimers/polymers.

The art as described in paragraph above, FIG. 1 can be utilized to convert the ethylene to octene/octene-1 in vapor phase operation as described above, with the same equipment.

The alternate option in FIG. 2 is provided, for Debutanizer Reactor Column configuration, which provides installing block catalyst beds in the column and this scheme is good for only n-butene feed conversion to octene.

Based on the configuration and feed compositions following conditions will be required for the Octene process for the FIG. 1 and FIG. 2.

FIG. 1:

| | |
|---|---|
| Stream 1, Inlet Temp(F.) | 100 (170 to 200 F. to Fractionator preferable) |
| Pressure (psig) | 100 to 120 Stream 1 |
| Fractionator overhead Presssure(psig) | 75 to 100 |
| LHSV (hr)$^{-1}$ | Reactor 2 to 10 (preferably 4 for each reactor) |
| Reactor Pressure (psig) | 370 to 400 |
| Reactor Temperature (F.) | 250 to 350 |
| Conversion | >95% to Octene |
| Purity Octene | >95% (can be improved by removal of trimers by distillation) |

FIG. 2

| | |
|---|---|
| Feed to Debutanizer Reactor | 185 to 200 F. (based on the temperature profile in the column) |
| Pressure overhead of Debutanizer Reactor Column (psig) | 300 to 400 |
| Pressure Octene Column (psig) | 60 to 100 |

Reaction Chemistry

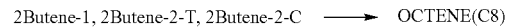

2Butene-1, 2Butene-2-T, 2Butene-2-C → OCTENE(C8)

Side Reaction

3Butene-1, 3Butene-2-T, 3Butene-2-C → Trimer (C12)

What RHT-Octene process claims is:

1. A method for producing octene/octene-1 comprising:
   (a) providing a feed stream comprising mixed $C_4$ hydrocarbons or ethylene;
   (b) passing the feed stream through an adsorption bed to remove any impurities from the feed stream and withdrawing an adsorption bed effluent stream;
   (c) heating the adsorption bed effluent stream;
   (d) passing the heated adsorption bed effluent stream to a fractionator;
   (e) withdrawing at least one side draw stream comprising n-butene from the fractionator;
   (f) passing the at least one fractionator side draw stream to a reactor, the reactor containing a catalyst suitable for the conversion of ethylene or $C_4$ hydrocarbons to octene;
   (g) withdrawing at least one reactor effluent stream comprising octene; and
   (h) feeding the at least one reactor effluent stream comprising octene to the fractionator.

2. The method of claim 1, wherein the catalyst is an acidic catalyst.

3. The method of claim 1, wherein the catalyst is either a zeolite or zeolite/Pt catalyst.

4. The method of claim 1, wherein the reactor is operated at a pressure in the range from about 350 psig to about 400 psig and a temperature in the range from about 250° F. to about 300° F.

5. The method of claim 1, wherein the reactor is operated in either upflow or downflow mode.

6. The method of claim 1, wherein the reactor is either a single phase or two phase reaction when the feed stream comprises n-butene.

7. The method of claim 1, wherein the reaction is a vapor phase reaction when the feed stream comprises ethylene.

8. A method for producing octene/octene-1 comprising:
   (a) providing a feed stream comprising mixed $C_4$ hydrocarbons;
   (b) passing the feed stream through an adsorption bed to remove any impurities from the feed stream and withdrawing an adsorption bed effluent stream;
   (c) heating the adsorption bed effluent stream;
   (d) passing the heated adsorption bed effluent stream to a debutanizer reactor column, the debutanizer reactor column containing multiple beds of catalyst suitable for the conversion of $C_4$ hydrocarbons to octene;
   (e) withdrawing an effluent stream comprising octene from the debutanizer reactor column; and
   (f) passing the effluent stream comprising octene to an octene separation column, wherein octene product is removed as a bottom stream and unconverted $C_4$ hydrocarbons are removed as an overhead stream;
   wherein upflowing vapor in the debutanizer reactor column bypasses at least one of the multiple beds of catalyst by way of a vapor bypass means.

9. The method of claim 8, wherein the catalyst is an acidic catalyst.

10. The method of claim 8, wherein the catalyst is either a zeolite or zeolite/Pt catalyst.

11. The method of claim 8, wherein the conversion of $C_4$ hydrocarbons to octene occurs at a pressure in the range from about 350 psig to about 400 psig and a temperature in the range from about 250° F. to about 300° F.

12. The method of claim 8, wherein the vapor bypass means comprises a chimney tray allowing for upflowing vapor to traverse the at least one bed of catalyst without coming into direct contact with the catalyst.

13. The method of claim 8, wherein the vapor bypass means comprises a transport line external to the debutanizer reactor column for routing the upflowing vapor around the at least one bed of catalyst.

* * * * *